(12) United States Patent
McKinley et al.

(10) Patent No.: US 10,307,184 B2
(45) Date of Patent: Jun. 4, 2019

(54) BONE FASTENER ASSEMBLY

(71) Applicant: Zimmer Biomet Spine, Inc., Westminster, CO (US)

(72) Inventors: Laurence McKinley, Escondido, CA (US); Michael Fulton, Superior, CO (US); Gregory Causey, Broomfield, CO (US); Jeffrey Thramann, Longmont, CO (US); Damon Belloni, Lakewood, CO (US); Terry Ziemek, Broomfield, CO (US); Alan Burkholder, Denver, CO (US)

(73) Assignee: Zimmer Biomet Spine, Inc., Westminster, CO (US)

( * ) Notice: Subject to any disclaimer, the term of this patent is extended or adjusted under 35 U.S.C. 154(b) by 406 days.

(21) Appl. No.: 14/624,031

(22) Filed: Feb. 17, 2015

(65) Prior Publication Data
US 2015/0157365 A1 Jun. 11, 2015

Related U.S. Application Data

(62) Division of application No. 11/972,894, filed on Jan. 11, 2008, now Pat. No. 8,961,568.
(Continued)

(51) Int. Cl.
*A61B 17/70* (2006.01)
(52) U.S. Cl.
CPC ...... *A61B 17/7037* (2013.01); *A61B 17/7038* (2013.01); *A61B 17/7032* (2013.01)
(58) Field of Classification Search
CPC ...................................... A61B 17/70–17/7046
See application file for complete search history.

(56) References Cited

U.S. PATENT DOCUMENTS

| 4,669,907 A | 6/1987 | Patton |
| 4,813,808 A | 3/1989 | Gehrke |

(Continued)

FOREIGN PATENT DOCUMENTS

| EP | 1354563 A2 | 10/2003 |
| FR | 2693365 A1 | 1/1994 |

(Continued)

OTHER PUBLICATIONS

"U.S. Appl. No. 11/972,894, Advisory Action dated Mar. 23, 2012", 3 pgs.
(Continued)

*Primary Examiner* — Nicholas J Plionis
*Assistant Examiner* — Steven J Cotroneo
(74) *Attorney, Agent, or Firm* — Schwegman Lundberg & Woessner, P.A.

(57) ABSTRACT

A bone fastener assembly for connecting a bone to a stabilizing construct includes a connecting member, a fastener seat, and a bone fastener. The connecting member includes a connecting member axis, a first opening, a second opening, and a first spherical surface. The connecting member axis extends from a proximal end to a distal end. The first opening is adjacent the proximal end. The second opening is adjacent the distal end. The fastener seat includes a first end, a second end, a passageway, and a second spherical surface. The passageway extends from the first end to the second end along a seat axis. The second spherical surface is configured to slidably engage the first spherical surface. The bone fastener includes a shank and a head. The shank extends though the passageway. The head engages a head-mating surface of the fastener seat.

20 Claims, 13 Drawing Sheets

Related U.S. Application Data

(60) Provisional application No. 60/909,891, filed on Apr. 3, 2007, provisional application No. 60/884,786, filed on Jan. 12, 2007.

(56) References Cited

U.S. PATENT DOCUMENTS

| | | | |
|---|---|---|---|
| 4,883,303 A | 11/1989 | Gross | |
| 5,102,412 A * | 4/1992 | Rogozinski | A61B 17/7082 606/250 |
| 5,588,329 A | 12/1996 | Nedachi | |
| 5,591,165 A | 1/1997 | Jackson | |
| 5,607,426 A | 3/1997 | Ralph et al. | |
| 5,645,599 A | 7/1997 | Samani | |
| 5,664,898 A | 9/1997 | Ferrari et al. | |
| 5,672,176 A | 9/1997 | Biedermann | |
| 5,728,098 A * | 3/1998 | Sherman | A61B 17/7032 606/269 |
| 5,810,818 A | 9/1998 | Errico et al. | |
| 5,954,725 A | 9/1999 | Sherman et al. | |
| 6,280,442 B1 | 8/2001 | Barker et al. | |
| 6,299,614 B1 | 10/2001 | Kretschmer et al. | |
| 6,478,798 B1 | 11/2002 | Howland | |
| 6,626,908 B2 | 9/2003 | Cooper et al. | |
| 6,716,214 B1 | 4/2004 | Jackson | |
| 6,974,460 B2 | 12/2005 | Carbone et al. | |
| 7,163,539 B2 | 1/2007 | Abdelgany et al. | |
| 7,186,255 B2 | 3/2007 | Baynham et al. | |
| 7,322,979 B2 * | 1/2008 | Crandall | A61B 17/7035 606/256 |
| 7,413,386 B2 | 8/2008 | Heindl et al. | |
| 7,559,714 B2 | 7/2009 | Ruhlander | |
| 7,588,593 B2 * | 9/2009 | Aferzon | A61B 17/7038 606/265 |
| 7,641,414 B1 | 1/2010 | Joyce | |
| 7,780,706 B2 * | 8/2010 | Marino | A61B 17/7037 606/264 |
| 7,896,902 B2 * | 3/2011 | Jeon | A61B 17/7032 606/246 |
| 7,951,172 B2 * | 5/2011 | Chao | A61B 17/7037 606/265 |
| 8,961,568 B2 | 2/2015 | McKinley et al. | |
| 2003/0032957 A1 * | 2/2003 | McKinley | A61B 17/7032 606/266 |
| 2003/0073995 A1 * | 4/2003 | Reed | A61B 17/6466 606/300 |
| 2003/0223805 A1 | 12/2003 | Ruhlander | |
| 2004/0153077 A1 | 8/2004 | Biedermann et al. | |
| 2004/0236330 A1 | 11/2004 | Purcell et al. | |
| 2005/0049589 A1 | 3/2005 | Jackson | |
| 2005/0080420 A1 * | 4/2005 | Farris | A61B 17/7037 606/261 |
| 2005/0187548 A1 * | 8/2005 | Butler | A61B 17/7032 606/278 |
| 2005/0203515 A1 * | 9/2005 | Doherty | A61B 17/7038 606/279 |
| 2005/0261687 A1 * | 11/2005 | Garamszegi | A61B 17/7011 606/305 |
| 2005/0277928 A1 | 12/2005 | Boschert | |
| 2006/0111715 A1 * | 5/2006 | Jackson | A61B 17/7037 128/897 |
| 2006/0129149 A1 | 6/2006 | Ott et al. | |
| 2006/0142761 A1 | 6/2006 | Landry et al. | |
| 2006/0149240 A1 * | 7/2006 | Jackson | A61B 17/7037 606/304 |
| 2006/0241769 A1 | 10/2006 | Gordon et al. | |
| 2006/0271046 A1 | 11/2006 | Kwak et al. | |
| 2006/0271047 A1 * | 11/2006 | Jackson | A61B 17/7037 606/304 |

FOREIGN PATENT DOCUMENTS

| | | |
|---|---|---|
| FR | 2734471 A1 | 11/1996 |
| FR | 2740674 A1 | 5/1997 |
| FR | 2789293 A1 | 8/2000 |
| JP | 2006504505 A | 2/2006 |
| WO | WO-0076413 A1 | 12/2000 |
| WO | WO-0197701 A1 | 12/2001 |
| WO | WO-2005018471 A1 | 3/2005 |
| WO | WO-2005122929 A1 | 12/2005 |
| WO | WO-2006052346 A2 | 5/2006 |
| WO | WO-2006057874 A2 | 6/2006 |
| WO | WO-2006127992 A2 | 11/2006 |
| WO | WO-2008089096 A2 | 7/2008 |

OTHER PUBLICATIONS

"U.S. Appl. No. 11/972,894, Examiner Interview Summary dated Nov. 25, 2011", 3 pgs.

"U.S. Appl. No. 11/972,894, Final Office Action dated Jun. 20, 2014", 10 pgs.

"U.S. Appl. No. 11/972,894, Final Office Action dated Dec. 9, 2011", 9 pgs.

"U.S. Appl. No. 11/972,894, Non Final Office Action dated Apr. 25, 2013", 9 pgs.

"U.S. Appl. No. 11/972,894, Non Final Office Action dated Jun. 22, 2011", 11 pgs.

"U.S. Appl. No. 11/972,894, Non Final Office Action dated Nov. 25, 2013", 9 pgs.

"U.S. Appl. No. 11/972,894, Notice of Allowance dated Oct. 20, 2014", 11 pgs.

"U.S. Appl. No. 11/972,894, Response filed Feb. 14, 2014 to Non Final Office Action dated Nov. 25, 2013", 11 pgs.

"U.S. Appl. No. 11/972,894, Response filed Mar. 9, 2012 to Final Office Action dated Dec. 9, 2011", 11 pgs.

"U.S. Appl. No. 11/972,894, Response filed May 16, 2011 to Restriction Requirement dated Mar. 10, 2011", 1 pgs.

"U.S. Appl. No. 11/972,894, Response filed Jul. 25, 2013 to Non Final Office Action dated Apr. 25, 2013", 12 pgs.

"U.S. Appl. No. 11/972,894, Response filed Sep. 17, 2014 to Final Office Action dated Jun. 20, 2014", 13 pgs.

"U.S. Appl. No. 11/972,894, Response filed Nov. 22, 2011 to Non Final Office Action dated Jun. 22, 2011", 11 pgs.

"U.S. Appl. No. 11/972,894, Restriction Requirement dated Mar. 10, 2011", 6 pgs.

"European Application Serial No. 08727610.1, Communication Pursuant to Article 94(3) EPC dated May 9, 2016", 5 pgs.

"European Application Serial No. 08727610.1, Extended European Search Report dated Jul. 5, 2012", 11 pgs.

"European Application Serial No. 08727610.1, Response filed Jan. 24, 2013 to Extended European Search Report dated Jul. 5, 2012", 12 pgs.

"International Application Serial No. PCT/US2008/059012, International Preliminary Report on Patentability dated Jul. 14, 2009", 6 pgs.

"International Application Serial No. PCT/US2008/059012, International Search Report dated Jul. 30, 2008", 1 pg.

"International Application Serial No. PCT/US2008/059012, Written Opinion dated Jul. 30, 2008", 5 pg.

"Japanese Application Serial No. 2009-545712, Office Action dated Sep. 11, 2012", W/ English Translation, 6 pgs.

"European Application Serial No. 08727610.1, Response filed Sep. 7, 2016 to Communication Pursuant to Article 94(3) EPC dated May 9, 2016", 55 pgs.

"European Application Serial No. 08727610.1, Communication Pursuant to Article 94(3) EPC dated Apr. 3, 2018", 5 pgs.

"European Application Serial No. 08727610.1, Response filed Jul. 11, 2018 to Communication Pursuant to Article 94(3) EPC dated Apr. 3, 2018", 13 pgs.

* cited by examiner

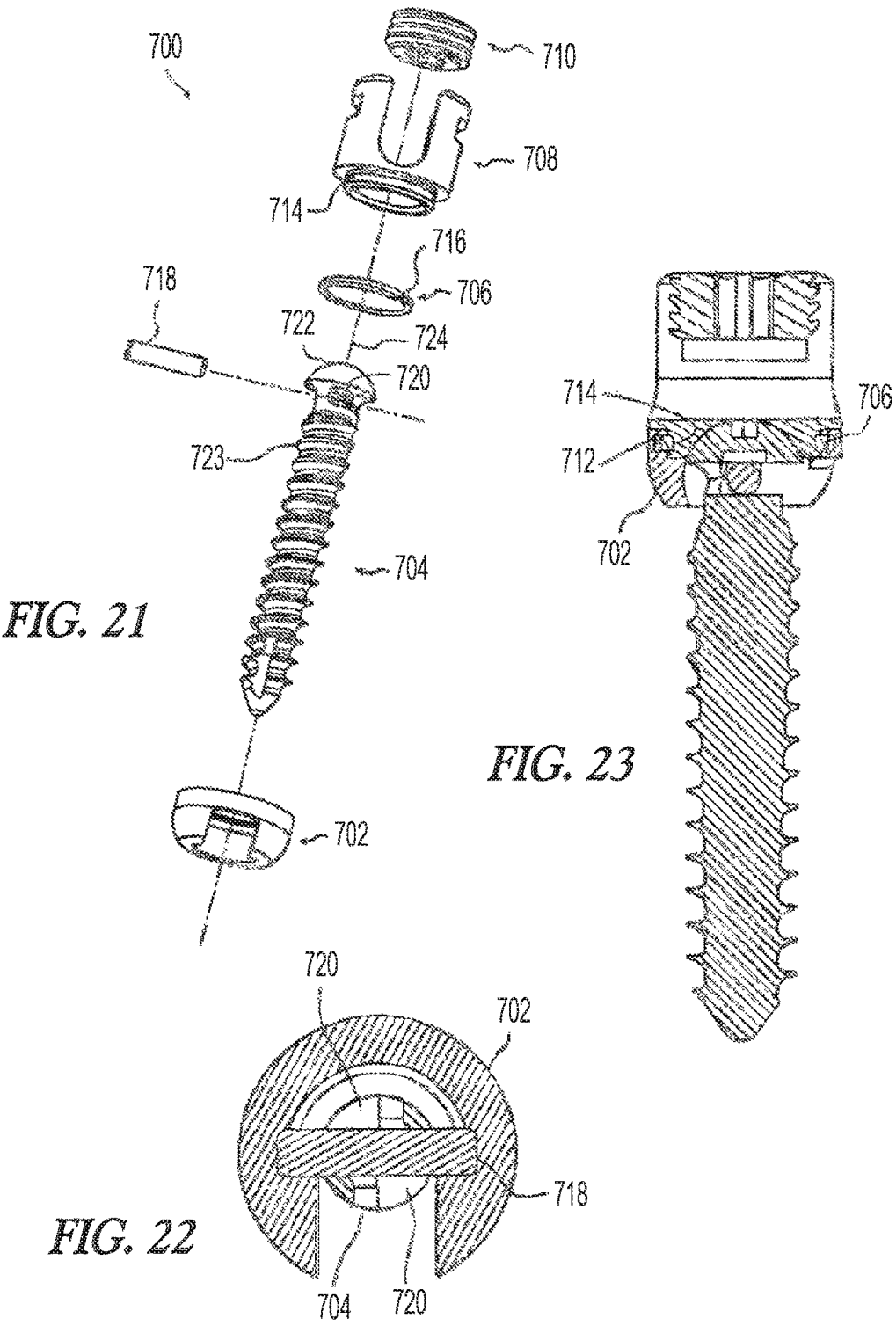

BONE FASTENER ASSEMBLY

CROSS-REFERENCE TO RELATED APPLICATIONS

This application is a divisional of U.S. patent application Ser. No. 11/972,894 filed on Jan. 11, 2008, which claims the benefit of U.S. Provisional Application No. 60/909,891 filed on Apr. 3, 2007, and U.S. Provisional Application No. 60/884,786 filed on Jan. 12, 2007. The entire disclosures of each of the above applications are incorporated herein by reference.

FIELD

The invention relates to medical fixation devices and more particularly to bone fastener assemblies useful in constructs for stabilizing bones of a patient.

BACKGROUND

This section provides background information related to the present disclosure which is not necessarily prior art.

A variety of orthopedic and neurological procedures make use of fasteners in constructs connecting one bone, or bone fragment, to another. For example, the connection of one vertebra of the human spine to another vertebra is a common beneficial procedure. The vertebrae of the human spine are arranged in a column with one vertebra on top of the next. An intervertebral disc lies between adjacent vertebrae to transmit force between the adjacent vertebrae and provide a cushion between them. The discs allow the spine to flex and twist.

With age, spinal discs begin to break down, or degenerate resulting in the loss, of fluid in the discs and consequently resulting in them becoming less flexible. Likewise, the disks become thinner allowing the vertebrae to move closer together. Degeneration may also result in tears or cracks in the outer layer, or annulus, of the disc. The disc may begin to bulge outwardly. In more severe cases, the inner material of the disc, or nucleus, may actually extrude out of the disc.

In a process known as spinal stenosis, the spinal canal may narrow due to excessive bone growth, thickening of tissue in the canal (such as ligamentous material), or both, The facet joints between adjacent vertebrae may degenerate and cause localized and/or radiating pain.

In addition to degenerative changes in the disc, the spine may undergo changes due to trauma from automobile accidents, falls, heavy lifting, and other activities.

The spine may also be malformed from birth or become malformed over time such as for example in cases of scoliosis, kyphosis, spondylosis, spondylolisthesis, and other deformities.

The conditions described above can result in disfigurement, pain, numbness, weakness, or even paralysis in various parts of the body. All of the above conditions and similar conditions are collectively, referred to herein as spine disease.

Typically, surgeons treat spine disease by attempting to stabilize adjacent vertebrae relative to one another and/or restore the normal, spacing between adjacent vertebrae to improve the shape of the spine and to relieve pressure on affected nerve tissue. Stabilizing the vertebrae is often accomplished with plates and/or rods attached to the vertebrae with fasteners such as screws such as for example pedicle screws. The stabilization may be rigid such that it eliminates motion between adjacent vertebrae and encourages bony fusion between the vertebrae or it may be dynamic to allow continued motion between the vertebrae. Often, the stabilization includes inserting a rigid spacer made of bone, metal, or plastic into the disc space between the adjacent vertebrae and allowing the vertebrae to grow together, or fuse, into a single piece of bone.

The patients anatomy- and/or the desired correction frequently require aligning the fastener at various angles relative to the bone and the rest of the stabilizing construct. Screws have been developed that are able to be angled relative to the stabilizing construct and they are typically referred to as "polyaxial" screws. However, despite the fact that numerous such polyaxial screw systems have been marketed, improvements are desirable. In particular, current devices provide limited angular adjustment.

SUMMARY

This section provides a general summary of the disclosure, and is not a comprehensive disclosure of its full scope or all of its features.

In one aspect, the present disclosure provides a bone fastener assembly for connecting a bone to a stabilizing construct. The bone fastener assembly includes a connecting member, a fastener seat, and a bone fastener. The connecting member includes a connecting member axis, a first opening, a second opening, and a first spherical surface. The connecting member axis extends from a proximal end to a distal end. The first opening is adjacent the proximal end. The second opening is adjacent the distal end. The fastener seat includes a first end, a second end, a passageway, and a second spherical surface. The passageway extends from the first end to the second end along a seat axis. The second spherical surface is configured to slidably engage the first spherical surface. The bone fastener includes a shank and a head. The shank extends though the passageway. The head engages a head-mating surface of the fastener seat.

In some configurations, the fastener seat may be insertable through the first opening and the bone fastener may be insertable through the second opening. The fastener seat may be movable from a first position to a second position. In the first position, the seat axis may be transverse to the connecting member axis after the fastener seat and bone fastener are inserted into the connecting member. In the second position, the seat axis may be parallel to the connecting member axis, and the fastener seat may engage the bone fastener and retain the bone fastener in the connecting member In some configurations, the fastener seat may comprise an outer edge and a notch extending radially outwardly from the passageway to the outer edge to receive the bone fastener as the fastener seat is moved from the first position to the second position.

In some configurations, the fastener seat may engage the connecting member in the second position in a pivoting relationship such that the fastener seat is able to pivot in at least one vertical plane containing the connecting member axis.

In some configurations, the fastener seat may engage the connecting member in the second position in a rotating relationship about the connecting member axis. The bone fastener may engage the fastener seat in pivoting relationship such that the bone fastener is able to pivot in at least one vertical plane containing the seat axis relative to the fastener seat to vary the angle between the bone fastener and the connecting member.

In some configurations, the bone fastener may be able to pivot relative to the fastener seat in only one vertical plane containing the seat axis.

In some configurations, the bone fastener may be able to pivot from a first position in which the shank and the seat axis are parallel, to a second position in which the shank is transverse to the seat axis. The bone fastener may be able to pivot in only one direction from the first position.

In some configurations, the fastener seat may include an outer edge and a notch extending radially outwardly from the passageway at least partway toward the outer edge. The notch may receive the bone fastener as the bone fastener pivots from the first position to the second position.

In some configurations, the head may include a third spherical surface and the fastener seat may include a complimentary mating fourth spherical surface.

In some configurations, the head may include a cylindrical surface and the fastener seat may include a complimentary mating cylindrical surface.

In some configurations, the fastener seat may include an elongated seating surface such that the bone fastener is engageable with the fastener seat in a pivoting relationship at a plurality of spaced apart locations.

In some configurations, the head may extend radially outwardly on opposite sides of the shank. The head may engage the fastener seat in the second position in a pivoting relationship with one degree of rotational freedom.

According to another aspect of the present disclosure, a bone fastener assembly for connecting a bone to a stabilizing construct is provided. The bone fastener assembly includes a rod holder, a fastener seat, and a bone fastener. The rod holder includes a first passage extending along a first axis from a proximal opening to a distal opening. The passage is partially defined by a first surface. The fastener seat includes a second passage extending along a second axis from a proximal end to a distal end. The distal end is at least partially defined by a second surface configured to mate with the first surface. The bone fastener includes a shank for engaging the bone, and a head. The shank defines a fastener axis. The fastener seat and the bone fastener are insertable within the rod holder. The fastener seat is movable along the first surface from a first position to a second position. In the first position, the second axis is transverse to the first axis after the fastener seat and bone fastener are inserted into the rod holder. In the second position, the second axis is parallel to the first axis, and the fastener seat engages the bone fastener and retains the bone fastener in the rod holder.

Further areas of applicability will become apparent from the description provided herein. The description and specific examples in this summary are intended for purposes of illustration only and are not intended to limit the scope of the present disclosure.

DRAWINGS

Various examples of the present invention will be discussed with reference to the appended drawings. These drawings depict only illustrative examples of the invention and are not to be considered limiting of its scope.

FIG. 21 is an exploded perspective view of another embodiment of a bone fastener assembly according to the present invention;

FIG. 22 is a top sectional view of the bone fastener assembly of FIG. 21;

FIG. 23 is aside sectional view of the bone fastener assembly of FIG. 21;

Corresponding reference numerals indicate corresponding parts throughout the several views of the drawings.

DETAILED DESCRIPTION

Example embodiments will now be described more fully with reference to the accompanying drawings.

Embodiments of a bone fastener assembly according to the present invention include a bone fastener and a connecting member mounted together to permit the fastener to pivot relative to a longitudinal axis of the assembly and swivel about the longitudinal axis. The fastener and connecting member mounting may be biased to permit a greater degree of pivoting of the fastener in one direction relative to the connecting member of they may be constrained to permit pivoting in only one direction. By biasing or selectively constraining the pivoting aspect of the fastener relative to the connecting member both the amount of pivoting in the preferential direction and the strength of the mounting may be increased. Due to the swiveling nature of the mounting between the fastener and connecting member, the maximum pivot position of the fastener relative to the connecting member may be oriented independently at any swivel position about the longitudinal axis of the assembly. This arrangement is therefore geometrically comprehensive with respect to the relative orientation of the fastener and connecting member.

The bone fastener may include a screw, pin, nail, bolt, staple, hook, and/or any other suitable fastener for engaging a bone.

The connecting member may include a plate engaging stud, rod holder, and/or any other suitable member for assembling a construct for stabilizing bones of a patient.

The mounting may include a ball and socket, hinge, spindle, and/or other suitable mountings.

While the specific embodiments used to illustrate the invention show the bone fastener assembly in the form of a pedicle screw useful to attach a rod to a vertebrae, the bone fastener assembly may connect to a bone in any of the variety of ways known in the art and may be utilized in any of the variety of constructs known in the art to stabilize bones at any location within the body.

Figure 1:
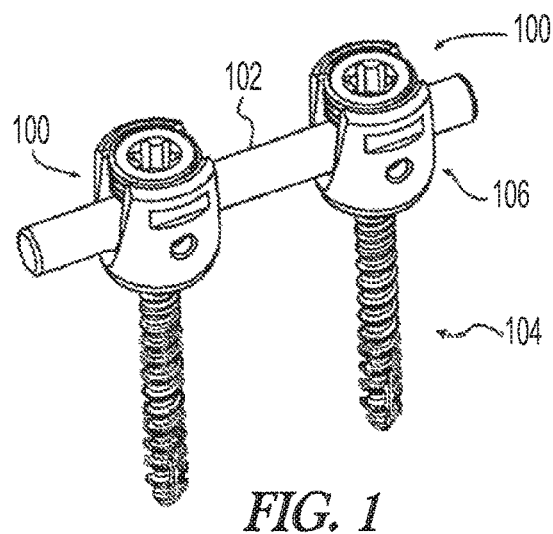
FIG. 1 is a perspective view of a bone fastener assembly according to the present invention.
Figure 2:
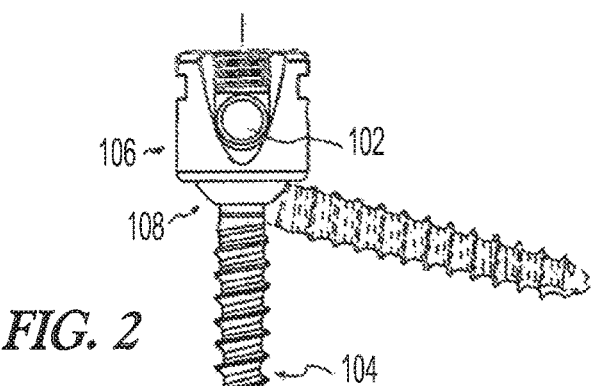
FIG. 2 is a side elevation view of the bone fastener assembly of FIG. 1.
Figure 3:
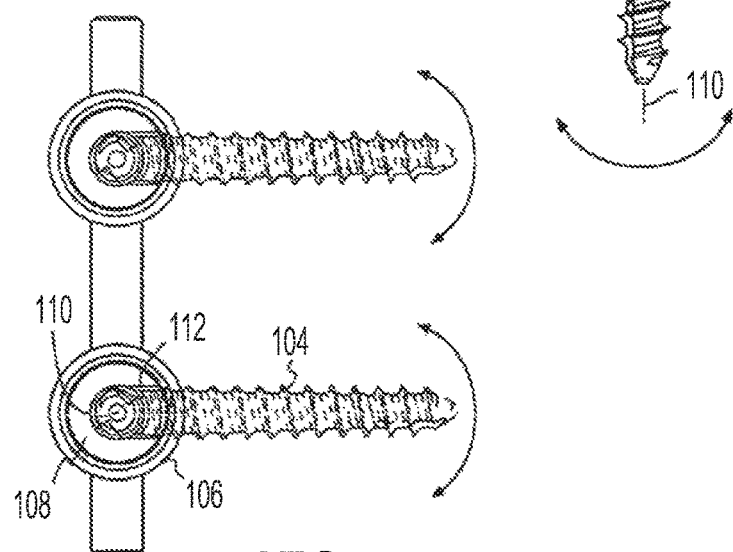
FIG. 3 is a bottom plan view of the bone fastener assembly of FIG. 1.

For example, FIGS. 1-3 illustrate a pair of bone fastener assemblies in the form of pedicle screw assemblies 100 coupled to a spinal rod 102 in order to fix adjacent vertebrae relative to the rod 102 and thereby stabilize the vertebrae relative to one another. Each pedicle screw assembly 100 includes a bone fastener in the form of a screw 104, a connecting member in the form of a rod holder 106, and a mounting in the form of a screw seat 108 (FIG. 2) linking the screw 104 and rod holder 106. The assembly includes a longitudinal axis 110 through the rod holder 106, screw seat 108, and screw 104.

As best seen in FIG. 2, the screw 104 is able to pivot in at least one vertical plane containing the longitudinal axis 110 to vary the angle between the screw 104 and rod holder 106. The screw seat 108 permits the screw 104 to pivot to an extreme angle in a preferential direction while maintaining support and strength by retaining material that limits pivoting in other directions. In the example of FIGS. 1-3, the screw seat 108 includes a notch 112 (FIG. 3) that permits the screw 104 to pivot preferentially into the notch 112. As best seen in FIG. 3, the screw 104 is also able to swivel about the longitudinal axis 110 in a horizontal plane transverse to the longitudinal axis 110 as the screw seat 108 rotates within the rod holder 106. This combination of vertical pivoting and horizontal swiveling allows the rod holder 106 to be swiveled to any desired position independently of the position of the notch 112 and screw 104 to selectively orient the position of maximum screw pivoting. Various mechanisms for achieving this motion are detailed below.

FIGS. 4-8 illustrate the details of one embodiment of the pedicle screw assembly 100 of FIG. 1. The pedicle screw assembly 100 includes a screw 104, a rod holder 106, a mounting in the form of a screw seat 108, a rod insert 114, and a set screw 116.

The screw 104 includes an elongated shank 118 having a tip 120 at a distal end, a head 122 at a proximal end, and a longitudinal axis 124 extending therebetween. A thread 126 spirals around the shank such that the screw 104 may be threaded into a bone. The head 122 may be cylindrical, conical, elliptical, spherical, and/or any other suitable shape. In the illustrative example of FIG. 4, the head 122 is generally spherical with a lower screw seat contacting portion 128 and an upper insert contacting portion 130.

The rod holder 106 includes a generally cylindrical body 132 having a longitudinal passageway 134 extending through the body 132 along an axis 136 from an upper or first opening 138 near a proximal end to a lower or second opening 140 near a distal end. The body 132 defines a screw seat contacting surface 142 adjacent the lower opening 140. The screw seat contacting surface 142 is preferably concave and spherical and has a diameter greater than the diameter of the lower opening 140. A transverse passageway 144 extends through the body 132 transverse to the axis 136 for receiving the rod 102 (FIG. 1). Preferably the transverse passageway 144 is open proximally to allow the rod 102 to be placed into the rod holder 106 with a proximal to distal motion. Alternatively the transverse passageway 144 may be closed proximally such that the rod 102 must be inserted transversely through the rod holder 106. A screw thread 146 spirals from the upper opening 138 distally into the rod holder body 132.

The screw seat 108 has a generally cylindrical body 148 with a lower, rod holder contacting surface 150. The rod holder contacting surface 150 is preferably convex and spherical such that it mates with the screw seat contacting surface 142 in relative pivoting relationship. A longitudinal passageway 152 extends through the body 148 along an axis 154 from an upper opening 156 near a proximal end to a lower opening 158 near a distal end. The body 148 defines a screw head seating surface 160 adjacent the lower opening 158. The screw head seating surface 160 is preferably concave and spherical. A notch 162 extends radially outwardly from the longitudinal passageway 152 and is sized to receive a portion of the screw shank 118. The notch 162 may extend only partway through the body 148 or it may extend completely through the body as shown in FIG. 4 and as will be discussed in more detail below.

The insert 114 has a generally cylindrical body 164 extending along a longitudinal axis 166 from an upper portion 168 near a proximal end to a lower, screw head contacting surface 170 near a distal end. The screw head contacting surface 170 preferably includes an axial hole 172 defining an annular seat 174. A transverse passageway 176 extends through the body 164 transverse to the axis 166 for receiving the rod 102. Preferably the transverse passageway 176 is open proximally to allow the rod 102 to be placed into the insert 114 with a proximal to distal motion. Alternatively the transverse passageway 176 may be closed proximally such that the rod 102 must be inserted transversely through the insert 114. The bottom of the transverse passageway 176 defines a rod contacting surface and is preferably concave and cylindrical.

The set screw 116 has a generally cylindrical body 178 about a longitudinal axis 180, a thread 182 spiraling around its exterior, and a driver engaging portion 184, in this example a multi-lobed opening. The set screw 116 is threadably receivable in the upper opening 138 of the rod holder 106.

Figure 4:
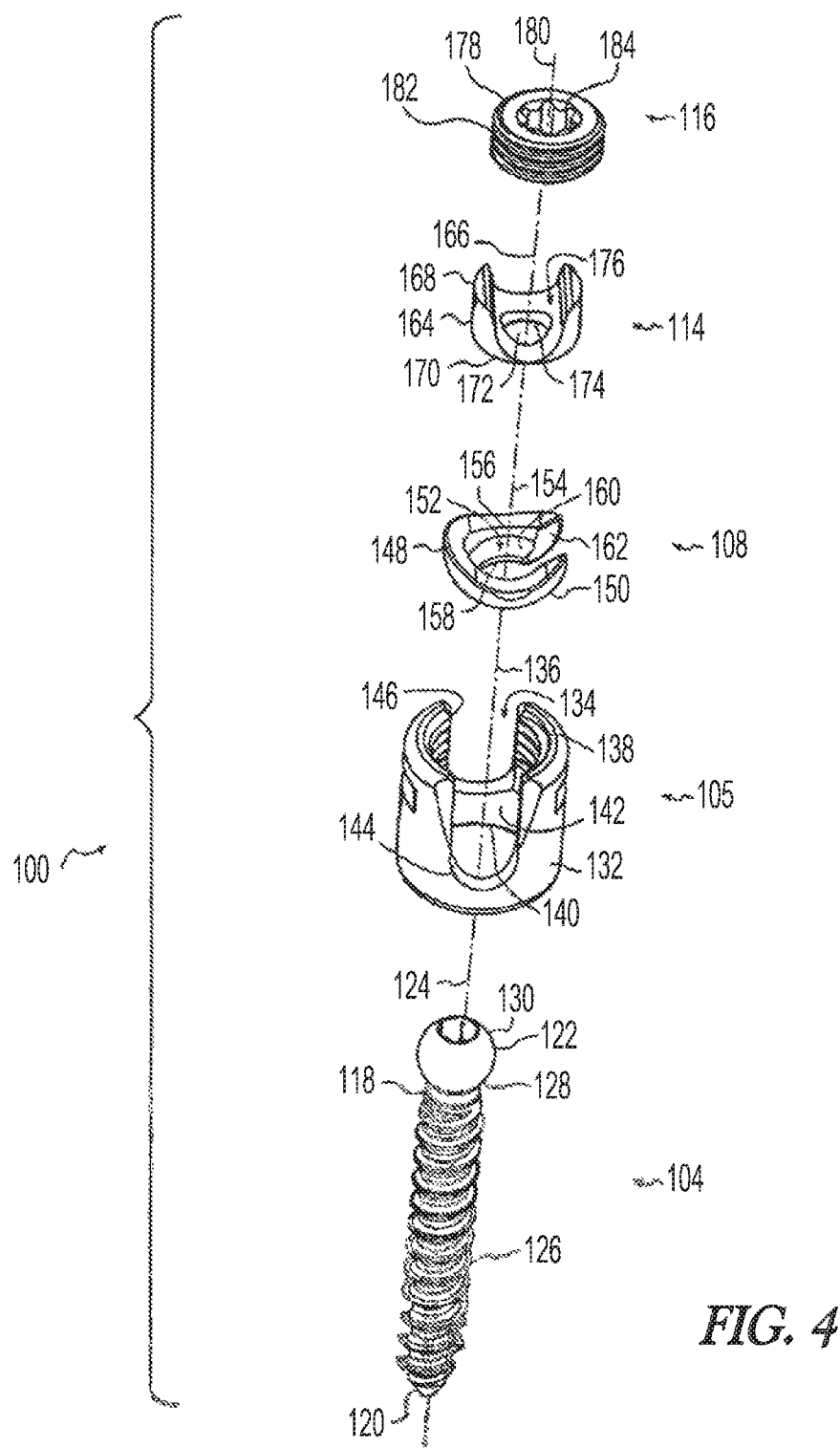
FIG. 4 is an exploded perspective view of the bone fastener assembly of FIG. 1.
Figure 5:
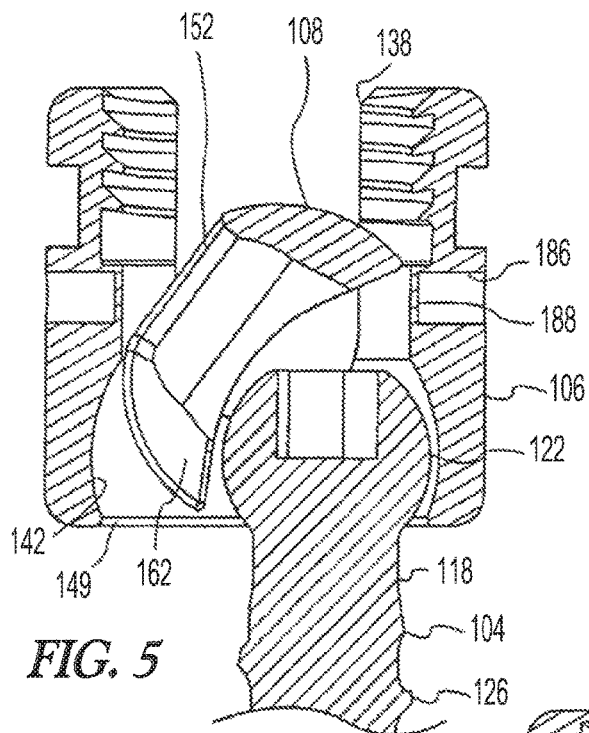
FIG. 5 is a side sectional view of the bone fastener assembly of FIG. 1.
Figure 6:
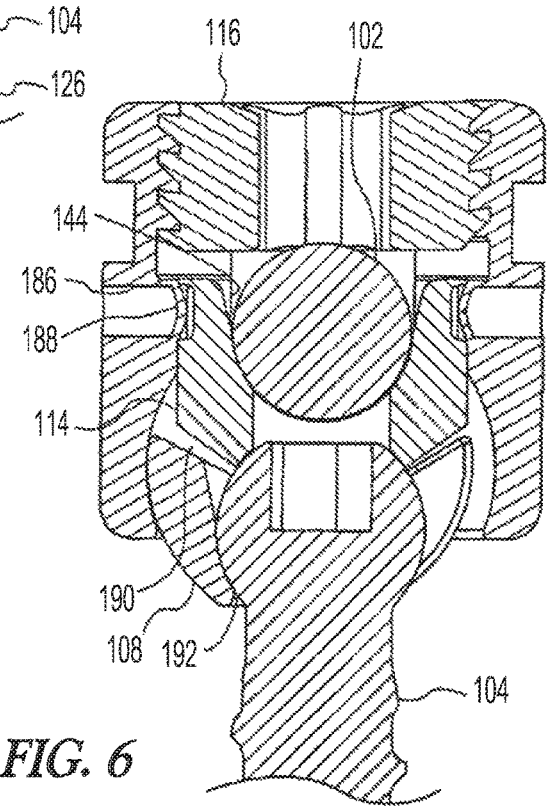
FIG. 6 is a side sectional view of the bone fastener assembly of FIG. 1.

FIGS. 5 and 6 Illustrate a method of assembling the components of FIG. 4. Referring to FIG. 5, the screw head 122 is inserted upwardly through the lower opening 140 of the rod holder 106. The screw seat 108 is tipped sideways and inserted through the upper opening 138 of the rod holder 106 with the notch 162 directed toward the screw head 122. As the screw seat 108 engages the screw seat contacting surface 142, the screw seat 108 is tipped upright so that the notch 162 slides under the screw head 122 and receives the screw shank 118. Preferably the passageway 152 and notch 162 are sized to fit closely around the screw shank 118 such that the screw 104 is only allowed to pivot in the direction of the notch and not transverse to the direction of the notch. Alternatively, for example in the case where the notch 162 does not extend all the way through the screw seat 108, the screw seat 108 may be positioned in the rod holder 106 and the screw 104 inserted through the upper opening 138 of the rod holder 106 and into the screw seat 108. However, in this alternative case, the passageway 152 through the screw seat would need to be enlarged enough to allow the screw thread 126 to pass.

Referring to FIG. 6, once the screw 104 and screw seat 108 are positioned in the rod holder 106, the insert 114 is placed over the screw 104 in preparation for receiving the rod 102. The screw 104, screw seat 108, and insert 114 may be assembled intraoperatively by the surgical team or they may be preassembled. Preferably the components are pre-assembled and locked in place to prevent disassembly in order to simplify their use in surgery. In the illustrative embodiment of FIGS. 4-8, the rod holder 106 includes a blind hole 186 defining a thin web 188 of material that is pressed inwardly to stake the insert 114 in the rod holder 106 to prevent disassembly.

During surgery, the screw 104 is driven into a bone, e.g. a pedicle, at a desired angle. The rod holder 106 is pivoted relative to the screw 104 to a desired angle with the screw 104 in the notch 162 and the rod holder 106 is swiveled relative to the screw seat 108 to a desired orientation to align the transverse passageway 144 with a desired rod orientation. The rod 102 is then placed into the transverse passageway 144 and the set screw 116 is threaded into the rod holder 106 to press the rod 102, insert 114, screw 104, screw seat 108, and rod holder 106 together to lock the construct in the desired position.

In the illustrative embodiment of FIGS. 4-8, the screw seat 108 and insert 114 are shaped to have a gap 190 between them and the screw seat 108 is relieved (as shown at 192 in FIG. 6) adjacent the screw shank 118 such that the screw seat 108 can pivot relative to the screw seat contacting surface 142 of the rod holder 106 and the screw shank 118 can pivot relative to the screw seat 108. This in effect produces a "double throw" action in which the screw 104 can pivot a first amount (FIG. 7) until the screw shank 118 abuts the screw seat 108 and the screw seat 108 abuts the insert 114 in most directions and a farther amount (FIG. 8) in the preferential direction of the notch 162 until it abuts the rod holder 106. The rod holder 106 may be notched to allow further pivoting in the preferred direction and/or the screw seat 108 may be extended to protrude former below the rod holder 106 to provide more pivoting before the screw shank 118 abuts the rod holder 106.

Figure 9:
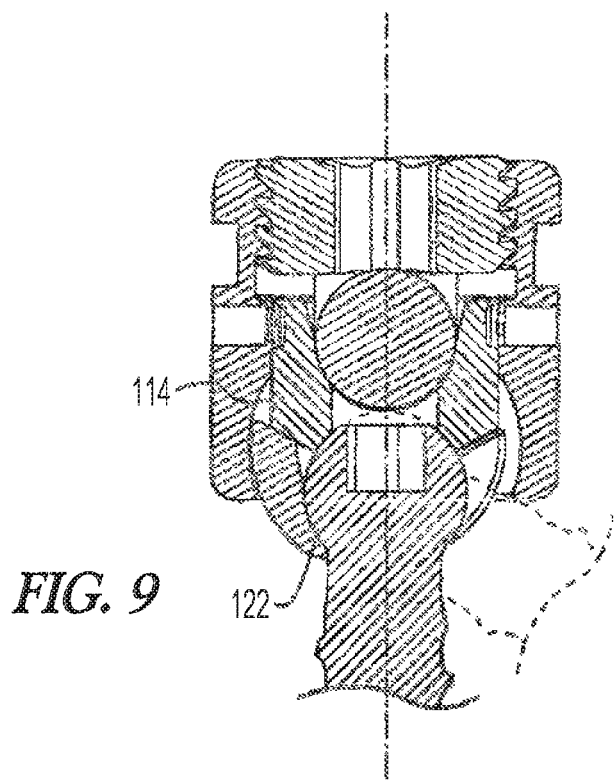
FIG. 9 is a side sectional view of the bone fastener assembly of FIG. 1 illustrating an alternative fit of the parts.

In the embodiment of FIG. 9, there are no gaps and the screw 104 can only pivot in the direction of the notch 162. In other words the screw 104 is pivotally constrained in all directions except in the direction of the notch 162. This "single throw" arrangement advantageously keeps the head 122 of the screw centered relative to the insert 114 for improved locking when the insert 114 is pressed against the screw head 122.

Figures 7, 8:
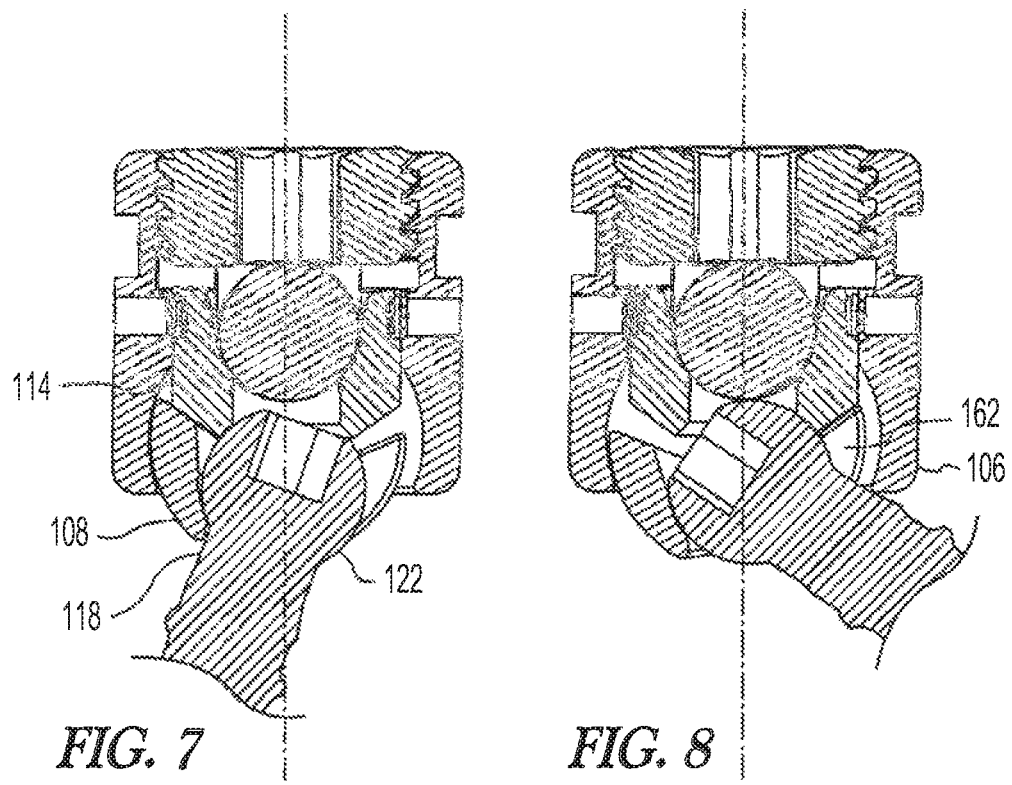
FIG. 7 is a side sectional view of the bone fastener assembly of FIG. 1.
FIG. 8 is a side sectional view of the bone fastener assembly of FIG. 1.
Figure 10:
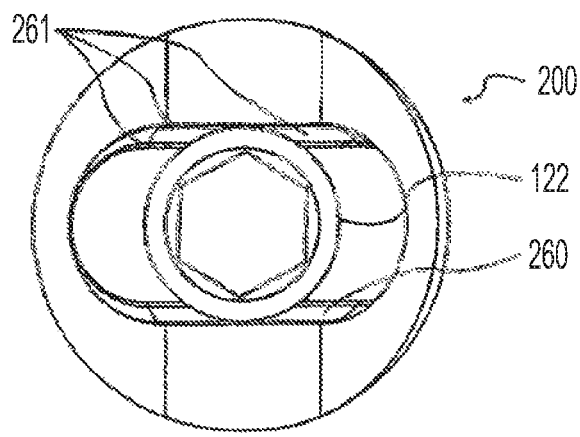
FIG. 10 is a top plan view of an alternative arrangement for the screw seat of FIG. 1.
Figure 11:
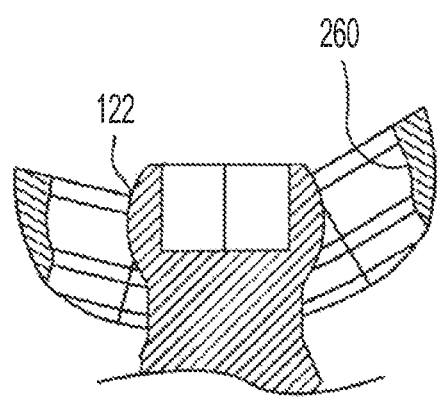
FIG. 11 is a partial side sectional view of the screw seat of FIG. 10.
Figure 12:
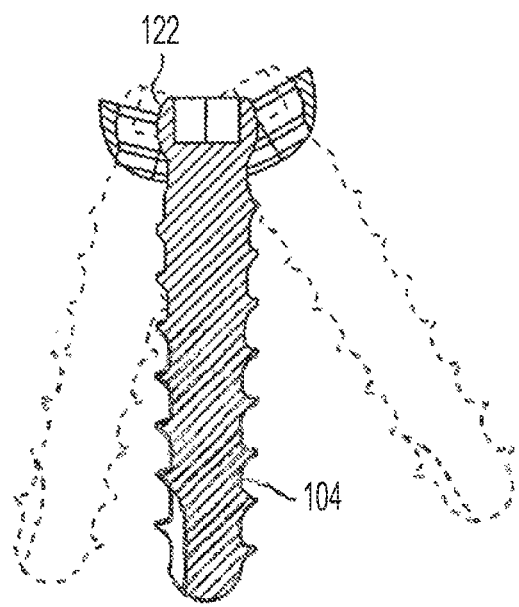
FIG. 12 is a side sectional view of the screw seat of FIG. 10.

FIGS. 10-12 illustrate an alternative screw seat 200 that is generally configured like, and operates like the screw seat 108 of FIGS. 4-8. Specifically, screw seat 200 differs from that of FIGS. 4-8, in that it has an elongated screw head seating surface 260 that allows the screw head 122 to slide along an arc and pivot at any position on the arc. Alternatively, the elongated screw head seating surface 260 may include a plurality of discrete head seating regions 261 allowing discrete ranges (FIG. 12) of screw angulation by selectively engaging the screw 104 with a preferred seating region. This may be advantageous in permitting additional pivoting range to the screw 104. It may also be advantageous in a "double throw" arrangement as shown in FIGS. 7-8 to allow the head 122 to slide relative to the seat 108 and stay centered relative to the insert 114 for improved locking.

Figure 13:
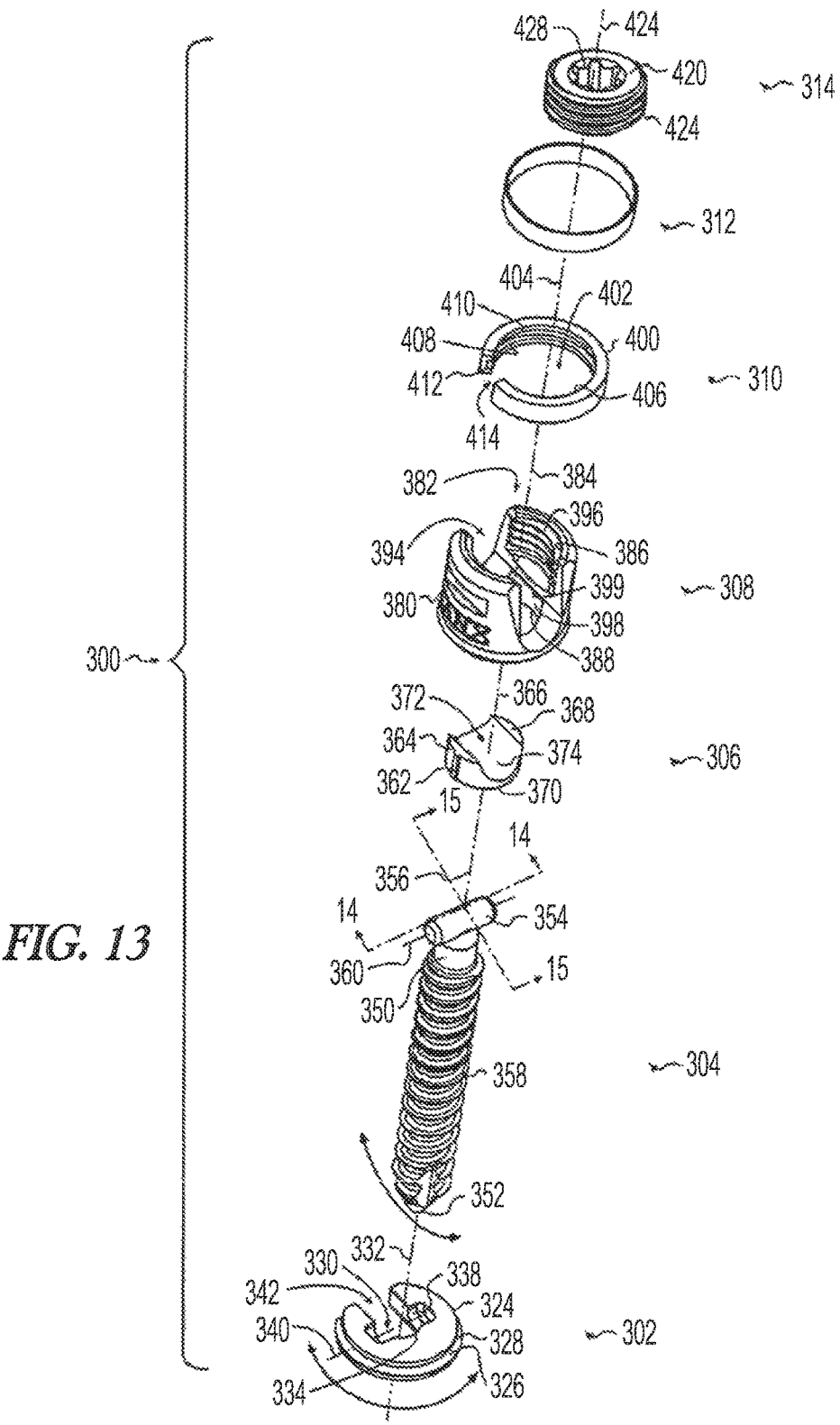
FIG. 13 is an exploded perspective view of another embodiment of a bone fastener assembly according to the present invention.
Figures 14, 15:
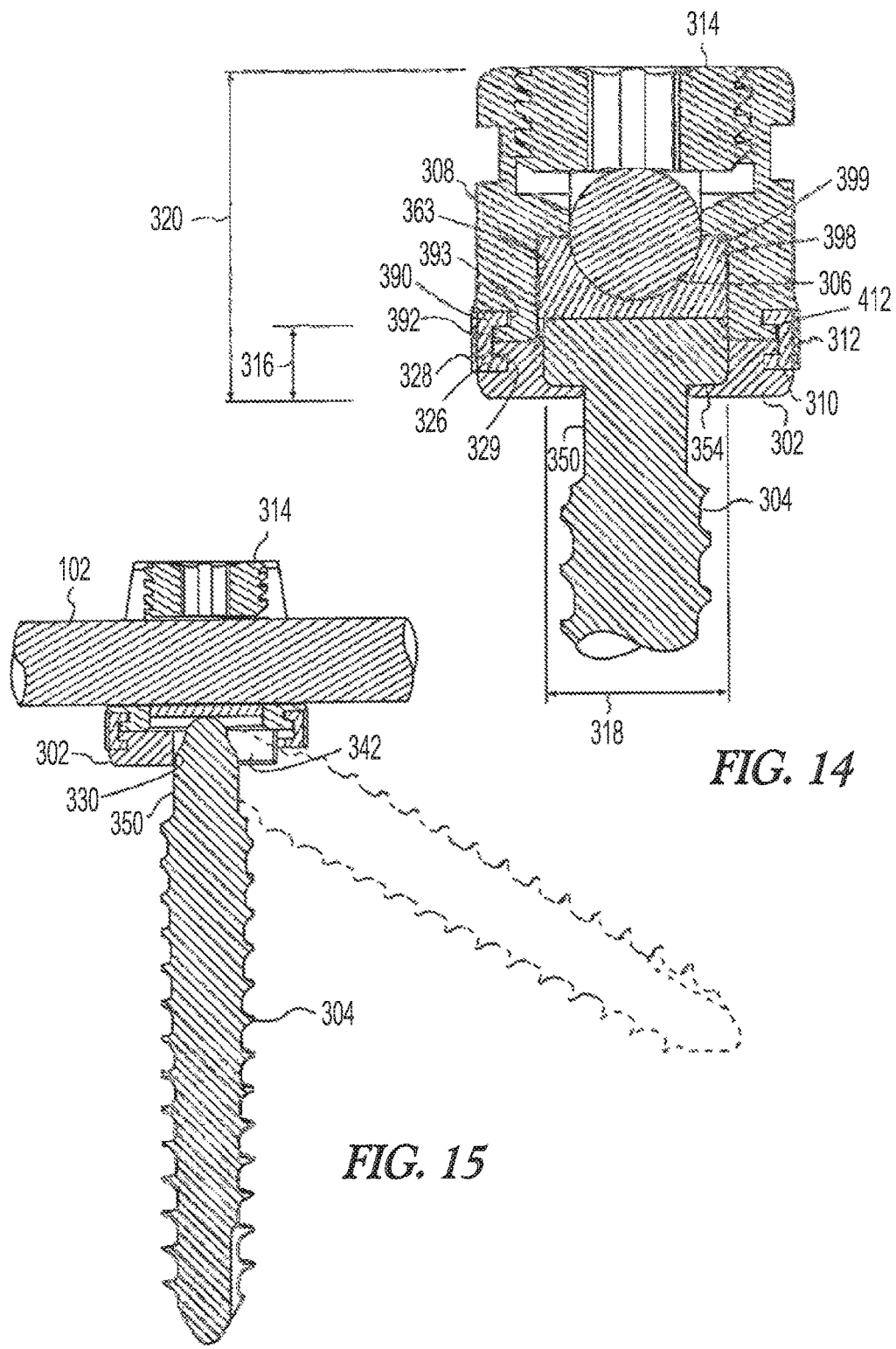
FIG. 14 is a partial side sectional view of the bone fastener assembly of FIG. 13.
FIG. 15 is a side sectional view of the bone fastener assembly of FIG. 13.

FIGS. 13-15 illustrate the details of another embodiment of a pedicle screw assembly like that of FIG. 1. In this embodiment, the screw has a transverse head (described more fully below) that engages the screw seat in hinge pivoting relationship. The transverse head in combination with the pivoting and swiveling aspects of the invention allow for a compact screw assembly presenting a low profile. As best seen in FIG. 14, the screw head has a small vertical height 316 relative to a large transverse width 318 and the overall vertical dimension 320 of the rod holder and screw head assembly is small. The low profile nature of the present invention is advantageous because it allows the pedicle screw assembly to be used in situations where traditional "poliyaxial" screws are not indicated because they cannot fit. The low profile nature of the present invention also provides aesthetic and comfort advantages by reducing the presence of protruding bumps under a patient's skin, especially in smaller and or thinner patients with less fleshy mass surrounding the screws. The transverse head arrangement of this embodiment permits a low profile while simultaneously more positively capturing the head and increasing the mechanical strength of the assembly. The pedicle screw assembly 300 includes a screw seat 302, a screw 304, an insert 306, a rod holder 308, a swivel ring 310, a retaining ring 312, and a set screw 314.

The screw seat 302 has a generally cylindrical body 324 defining a proximally facing shoulder 326, a rim 328, and an undercut 329 (FIG. 14). A longitudinal passageway 330 extends through the body along an axis 332 from an upper opening 334 near a proximal end to a lower opening near a distal end. The body defines a screw head contacting surface 338 extending distally into the body 324. The screw head contacting surface 338 may be cylindrical, conical, elliptical, spherical, and/or any other suitable shape. In the illustrative example of FIGS. 13-15, the screw head contacting surface 338 includes bilateral cylindrical depressions formed in the body on either side of the longitudinal passageway 330 and aligned along an axis 340 transverse to the longitudinal axis 332. A notch 342 extends outwardly from the longitudinal passageway 330 and is sized to receive a portion of the screw 304. The notch 342 may extend only partway through the body 324 or it may extend completely through the body 324 as shown in FIG. 13.

The screw 304 includes an elongated shank 350 having a tip 352 at a distal end, a head 354 at a proximal end, and a longitudinal axis 356 extending therebetween. A thread 358 spirals around the shank 350 such that the screw 304 may be threaded into a bone. The head may be cylindrical, conical, elliptical, spherical, and/or any other suitable shape to cooperatively engage head contacting surface 338. In the illustrative example of FIG. 13, the head is generally cylindrical and projects outwardly transverse to the screw shank along an axis 360. The screw is generally "T"-shaped and the head 354 is sized to engage the screw head contacting surface 338 of the screw seat 302 with the axes 340, 360 coaxially aligned such that the screw may pivot about the axes 340, 360 with the shank 350 moving in the longitudinal passageway 330 and notch 342.

The insert 306 has a generally cylindrical body 364 extending along a longitudinal axis 366 from an upper portion 368 near a proximal end to a lower, screw head contacting surface 370 near a distal end. A transverse passageway 372 extends through the body transverse to the axis 366 for receiving the rod 102. Preferably the transverse passageway 372 is open proximally to allow the rod 102 to be placed into the insert 306 with a proximal to distal motion. Alternatively the transverse passageway 372 may be closed proximally such that the rod 102 must be inserted transversely through the insert 306. The bottom of the transverse passageway 372 defines a rod contacting surface 374 and is preferably concave and cylindrical. The body includes a longitudinal rib 362 that engages a corresponding groove 363 (FIG. 14) in the rod holder 308 to orient the transverse passageway 372 relative to the rod holder 308.

The rod holder 308 includes a body 380 having a longitudinal passageway 382 extending through the body 330 along an axis 384 from an upper or first opening 386 near a proximal end to a lower or second opening 388 near a distal end. The lower opening 388 is sized to receive the insert 306 and screw head 354. The body 380 defines a distally facing shoulder 390, a rim 392, and an undercut 393 extending into the body 380 (FIG. 14). A transverse passageway 394 extends through the body 380 transverse to the axis 384 for receiving the rod 102. Preferably the transverse passageway 394 is open proximally to allow the rod 102 to be placed Into the rod holder 308 with a proximal to distal motion. Alternatively the transverse passageway 394 may be closed proximally such that the rod 102 must be inserted transversely through the rod holder 308. A screw thread 396 spirals from the upper opening 386 distally into the rod holder body 380. The body 380 defines an enlarged cavity 398 for receiving the insert 306. The cavity 398 defines an internal distally facing shoulder 399 against which the upper portion 368 of the insert 306 abuts to trap the insert 306 in the cavity 398 between the rod holder 308 and screw seat 302.

The swivel ring 310 includes a generally cylindrical body 400 having a longitudinal passageway 402 extending through the body 400 along an axis 404 from an upper or first opening 406 near a proximal end to a lower or second opening 408 near a distal end and defining an inner surface 410. The swivel ring 310 has an outer diameter and an inner diameter. The swivel ring 310 includes an internal annular groove 412 extending into the body 400 from the inner surface 410 radially outwardly. The swivel ring 310 is interrupted by a notch 414 so that the swivel ring 310 can be elastically deformed to change the inner and outer diameters. The inner diameter and annular groove 412 are sized to engage the rims and undercuts of the screw seat 302 and rod holder 308 as will be explained further below.

The retaining ring 312 comprises a generally cylindrical hollow ring having an internal diameter sized to press lit around the swivel ring 310.

The set screw 314 has a generally cylindrical body 420 about a longitudinal axis 424, a thread 426 spiraling around its exterior, and a driver engaging portion 428. The set screw 314 is threadably receivable in the upper opening 386 of the rod holder 308, FIGS. 14 and 15 illustrate the pedicle screw assembly 300 of FIG. 13 in cross section. To assemble the pedicle screw assembly 300, the screw head 354 is seated in the screw seat 302. The insert 306 is placed in the cavity 398 of the rod holder 308 and the top of the screw seat 302 is abutted with the bottom of the rod holder 308. The swivel ring 310 is sprung open so that it can be slipped over the rod holder 308 and screw seat 302. The swivel ring is snapped into place with the rims 328, 392 of the screw seat 302 and rod holder 308 captured in the groove 412. The retaining ring 312 is then pressed into place around the swivel ring 310 to prevent the swivel ring 310 from springing open and releasing the screw seat 304 and rod holder 308. The screw seat 302 and rod holder 308 are free to rotate relative to one another about a longitudinal axis and the screw 304 is free to pivot relative to the screw seat 302 about a transverse axis. The "T"-head configuration of the screw 304 and screw seat 302 creates a hinge joint between them constraining the screw 304 and screw seat 302 to one degree of rotational freedom relative to one another. In the embodiment of FIGS. 13-15, the screw shank 350 abuts the side of the longitudinal passageway 330 to prevent the screw 304 from pivoting to the left in FIG. 15. The screw 304 can pivot freely to the right in FIG. 15 and into the notch 342 to an extreme pivot angle. The pivot angle can be increases further by extending the screw seat 302 further distally to deepen the notch 342 to receive more of the screw 304. Pivot angles of 90 degrees or more are easily obtainable with such a modification. Conversely, the shallow screw seat of FIGS. 13-15 provide for a more compact, low profile assembly.

During surgery, the screw 304 is driven into a bone, e.g. a pedicle, at a desired angle. The rod holder 308 is pivoted relative to the screw 304 to a desired angle with the screw 304 in fee notch 342 and the rod holder 308 is swiveled relative to the screw seat 302 to a desired orientation to align the transverse passageway 394 with a desired rod orientation. The rod 102 is then placed Into the transverse passageway 394 and the set screw 314 is threaded into the rod holder 308 to press the rod 102, insert 306, screw 304, screw seat 302, and rod holder 308 together to lock the construct in the desired position.

Figure 16:
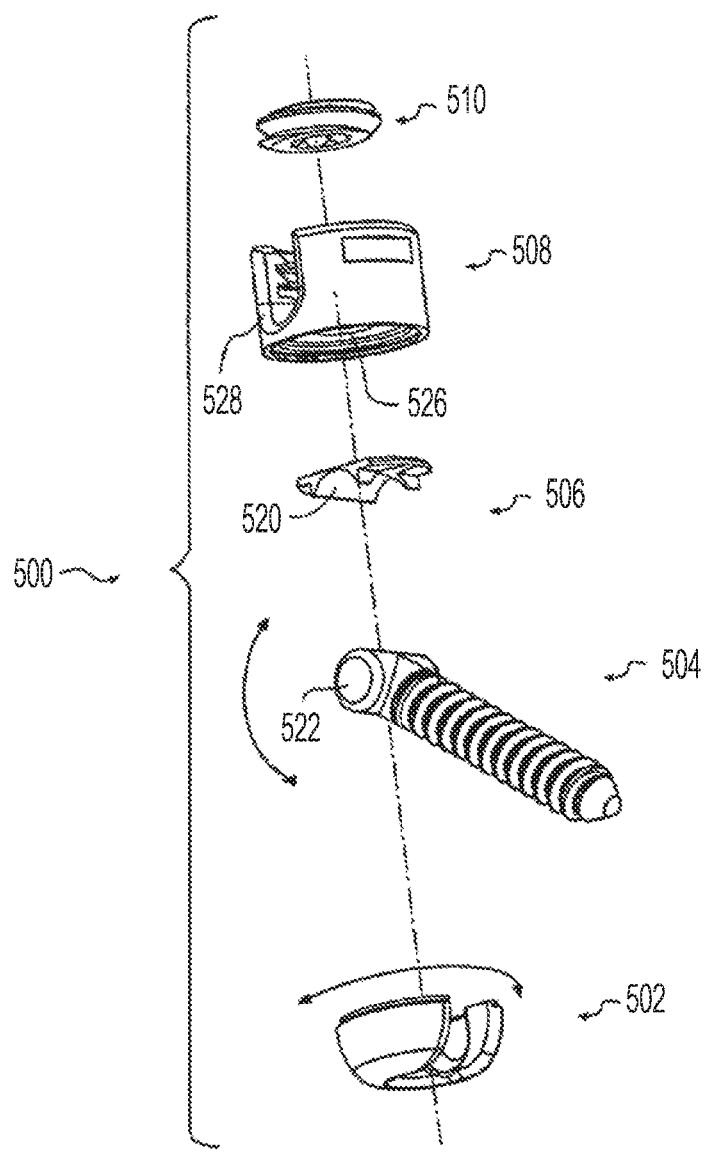
FIG. 16 is an exploded perspective view of another embodiment of a hone fastener assembly according to the present invention.
Figure 17:
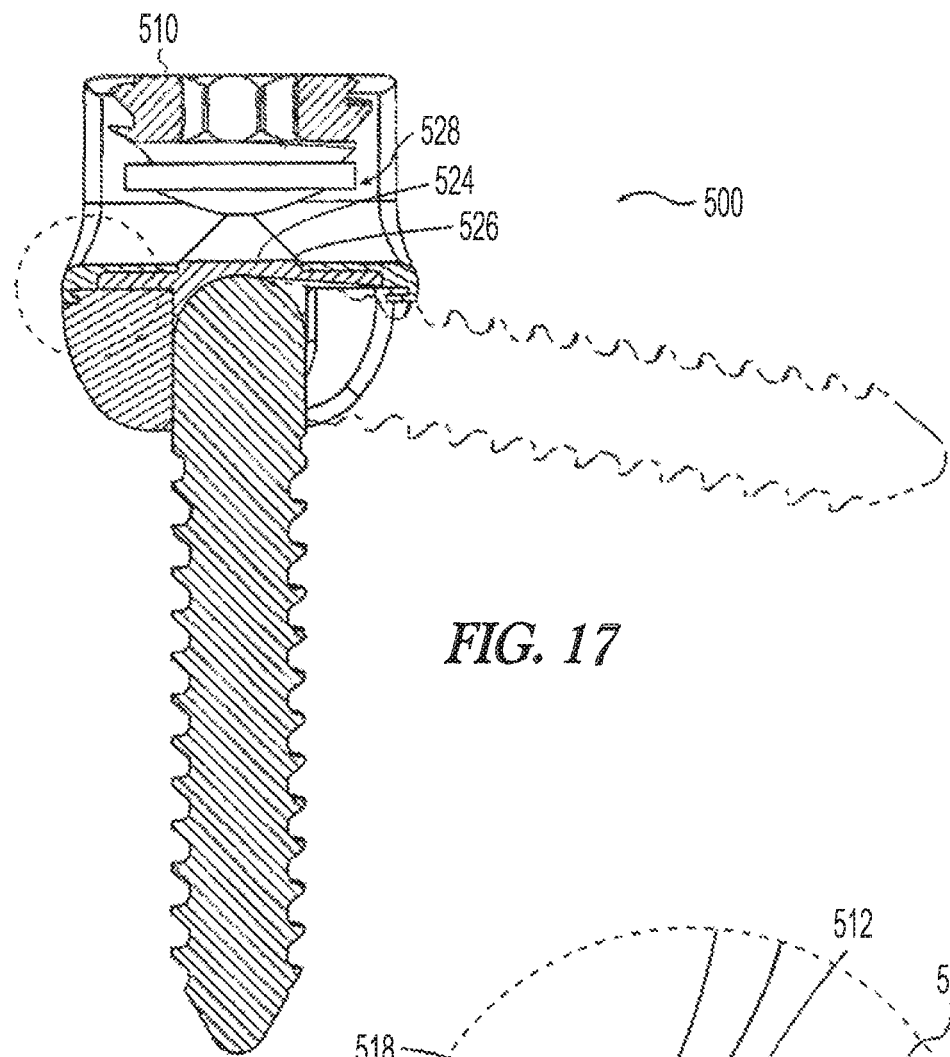
FIG. 17 is a side sectional view of the bone fastener assembly of FIG. 16.
Figure 18:
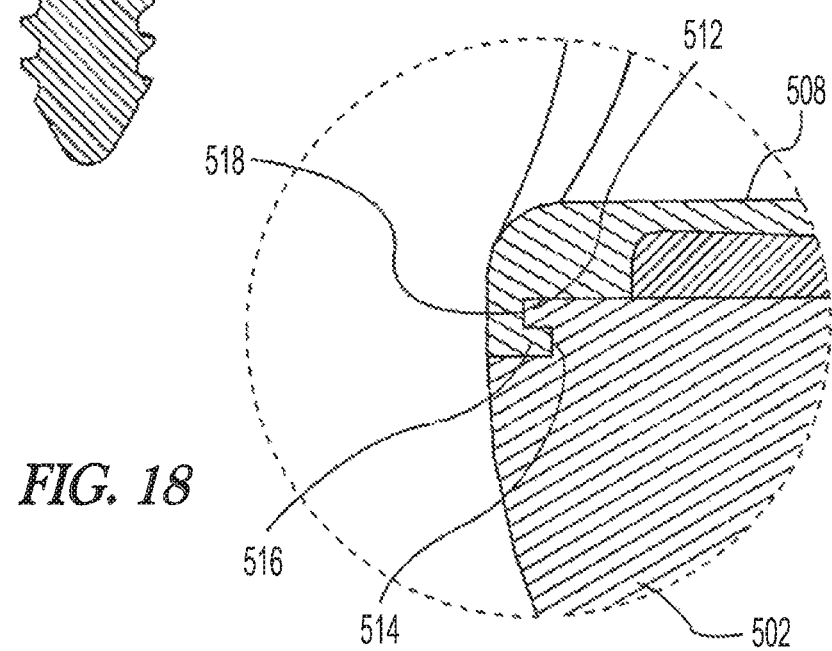
FIG. 18 is a detail view of the side sectional view of FIG. 17.

FIGS. 16-18 illustrate the details of another embodiment of a pedicle screw assembly 500 like that of FIG. 1. The pedicle screw assembly 500 of FIGS. 16-18 is similar to that of FIGS. 13-15 in that it includes a screw seat 502, a "T"-shaped screw 504, an insert 506, a rod holder 508, and a set screw 510. However, the pedicle screw assembly 500 of FIGS. 16-18 differs from that of FIGS. 13-15 in that instead of having a swivel ring and retaining ring to capture and hold the screw seat 502 and rod holder 508 together, the screw seat 502 and rod holder 508 snap together directly. The screw seat 502 is in the form of a lower shell having a rim 512 and an undercut 514 and the rod holder 508 is in the form of an upper shell having a rim 516 and an undercut 518 (FIG. 18). The screw seat 502 and rod holder 508 snap together with the rim of one fitting into the undercut of the other. The insert 506 of the embodiment of FIGS. 16-18 also differs from the insert 306 of the embodiment of FIGS. 13-15. The insert 506 has a cylindrical concave lower surface 520 shaped to receive the cylindrical head 522 of the screw 504 (FIG. 16). The insert 506 also has a cylindrical boss 524 (FIG. 17) that projects upwardly through a central longitudinal passageway 526 into a transverse rod receiving passageway 528. When a rod 102 is placed in the pedicle screw assembly 500 and the set screw 510 is tightened, the rod 102 presses against the boss 524 which forces the insert 506 against the screw head 522 to lock the construct in position. Note that the embodiment of FIGS. 16-18 is shown with a relatively deep screw seat 502 and correspondingly deep screw receiving notch to permit high pivot angles.

Figures 19, 20:
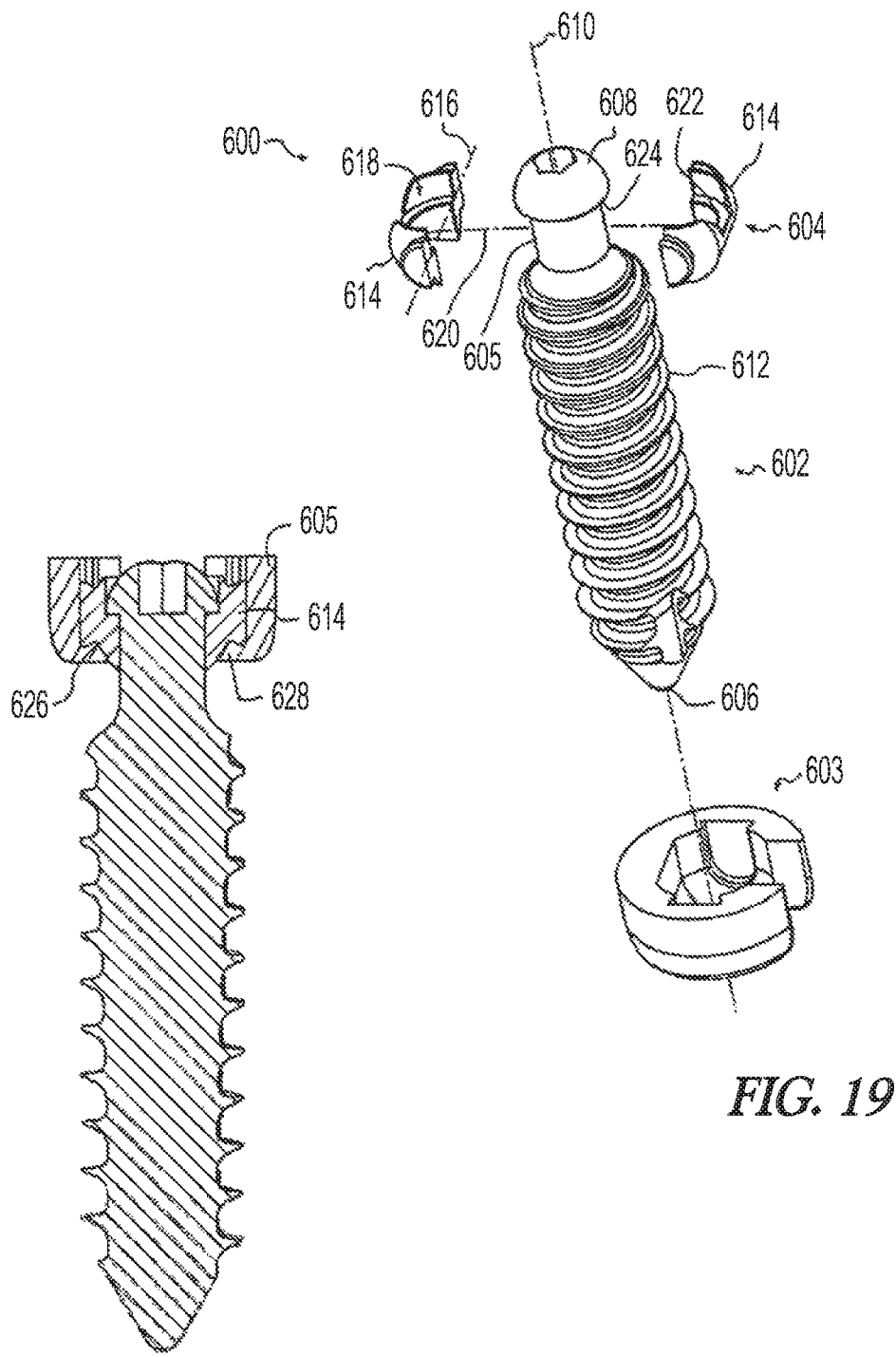
FIG. 19 is an exploded perspective view of an alternative arrangement for the bone screw of FIGS. 13-17.
FIG. 20 is a side sectional view of the embodiment of the bone screw of FIG. 19.

One of the characteristics of the embodiments of FIGS. 13-18 is that the screw and screw seat do not swivel about the longitudinal axis relative to one another so that in order to orient the direction of preferential screw pivoting, e.g. the notch, relative to the bone, the screw is threaded into or out of the bone. Generally a preferred orientation of the notch can be achieved within a half turn in either direction so that the change in screw depth is minimal FIGS. 19-20 illustrate a screw assembly 600 that can be substituted for the screw in the embodiments of FIGS. 13-18 to permit adjustment of the direction of preferential screw pivoting independent of screw depth. The screw assembly 600 includes a screw 602, a separate modular "T"-head 604, and a screw seat 603. The screw 602 includes an elongated shank 605 having a tip 606 at a distal end, a head 608 at a proximal end, and a longitudinal axis 610 extending therebetween. A thread 612 spirals around the shank 605 such that the screw 602 may be threaded into a bone. The "T"-head 604 includes a generally cylindrical body 614 oriented along a head axis 616 and a passageway 618 through the body 614 transverse to the head axis 616. The "T"-head 604 is preferably an assembly of two half heads that are assembled to a reduced portion of the shank 605 transverse to the longitudinal axis 610. By making the "T"-head 604 in two halves, the screw head 608 and "T"-head 604 can be made more compact since the passageway and screw head 608 can have a smaller diameter than the thread 612. However, a one-piece "T"-head 604 is within the scope of the invention with the diameter of the passageway 618 and head 608 sized accordingly. A countersunk seat 622 is formed coaxially with the passageway 618 to receive the screw head 608. A lower surface 624 of the screw head 608 abuts the seat 622 to prevent the screw 602 from passing through the "T"-head 604. With the screw 602 received in the passageway 618 of the "T"-head 604, the assembly 600 of FIG. 19 may be substituted for the "T"-shaped screws 304, 504 of FIGS. 13-17 to permit the screw seat 302, 502 (along with the "T"-head 604) to be rotated about the axis 610 without the need to rotate the screw shank 605 relative to the bone. Thus, the orientation of preferential screw pivoting may be adjusted without changing the depth of the screw 602 in the bone. The "T"-head of FIGS. 19-20 optionally includes an annular groove 626 formed about the head axis 616 on each side of the body 614. As best seen in FIG. 20, the groove 626 captures a portion 628 of the screw seat 605 on each side to prevent the screw seat 605 from splaying open when forces are applied to the pedicle screw assembly 600.

FIGS. 21-23 illustrate the details of another embodiment of a pedicle screw assembly 700 like that of FIG. 1, The embodiment of FIGS. 21-23 includes a screw seat 702, a "T"-shaped screw assembly 704, a locking ring 706, a rod holder 708, and a set screw 710. The assembly of the screw seat 702 and rod holder 708 is similar to the embodiment of FIG. 16 except that the screw seat 702 and rod holder 708 of FIG. 21 are locked with a locking ring 706 rather than snapping directly together. The screw seat 702 includes a groove 712 and the rod holder 708 includes a groove 714 each sized to receive a portion of the locking ring 706. The locking ring 706 includes a notch 716 allowing it to be elastically expanded and contracted. The locking ring 706 is first assembled onto one of the components, e.g. it can be snapped into the groove 712 in the screw seat 702. The rod bolder 708 is then pressed into the screw seat 702 causing the locking ring 706 to expand until the grooves 712, 714 are aligned and the locking ring 706 contracts to reside partially in each groove 712, 714 and lock the rod holder 708 and screw seat 702 together for relative rotation.

The "T"-shaped screw assembly 704 of FIGS. 21-23 permits orientation of the preferential screw pivot direction without changing the depth of the screw assembly 704 in the bone similar to the embodiment of FIG. 19-20. However, in the embodiment of FIGS. 21-23 the "T"-shaped screw assembly 704 includes a pin 718 inserted transversely through a passageway 720 in a head 722 of a screw 723. The passageway 720 is rotationally enlarged about the longitudinal axis 724 so that pin 718 and screw 723 are able to rotate relative to one another about the longitudinal axis 724. Thus, when the pin 718 is seated in the screw seat 702, the screw seat 702 and pin 718 can rotate about the screw 723.

The embodiment of FIGS. 21-23 also differs from the other embodiments in that there is no insert and the rod 102 (not shown in FIGS. 21-23) bears directly on the screw head 722.

Figures 24, 25:
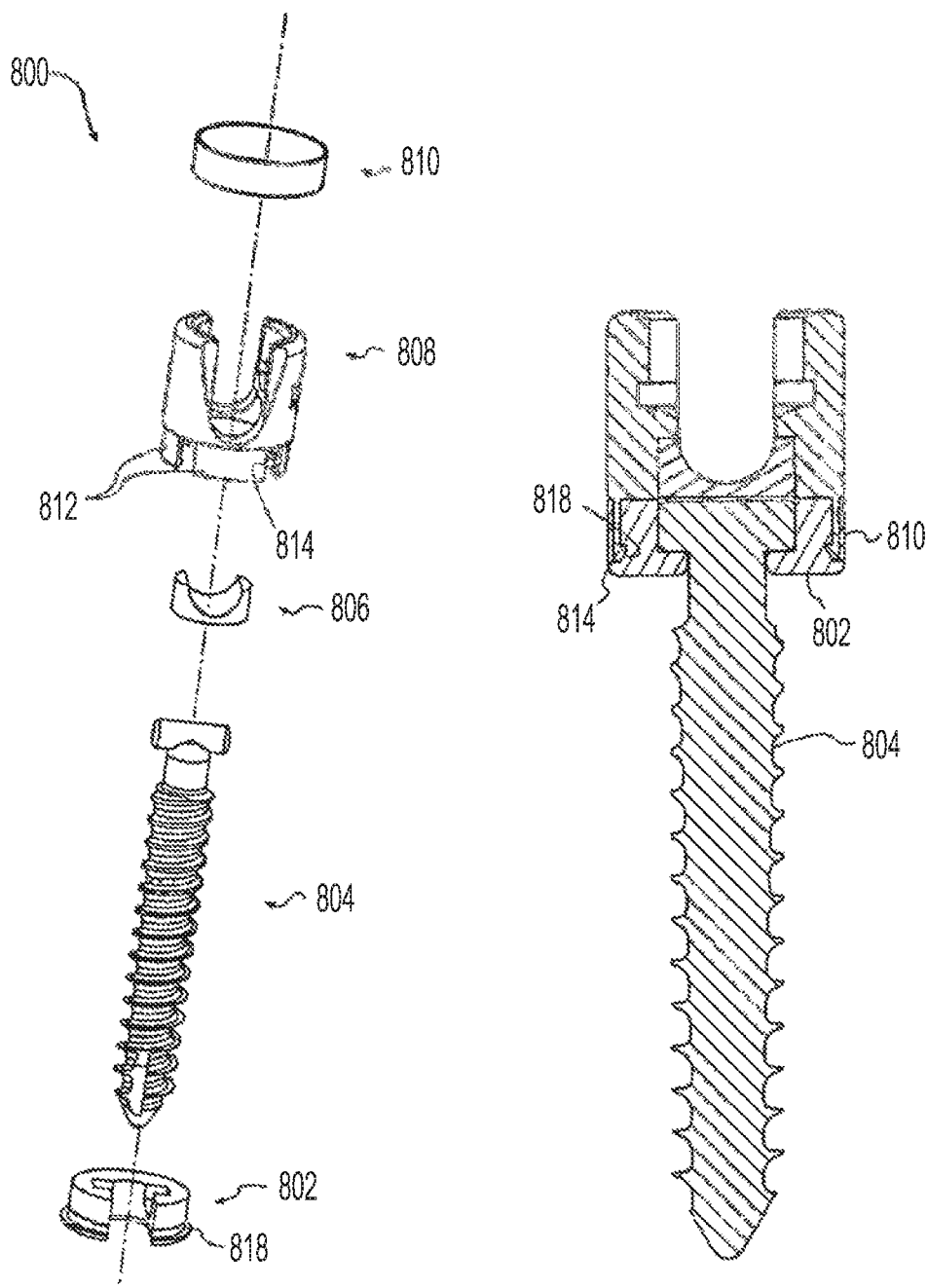
FIG. 24 is an exploded perspective view of another embodiment of a bone fastener assembly according to the present invention.
FIG. 25 is side sectional view of the bone fastener assembly of FIG. 24.

FIGS. 24-25 illustrate the details of another embodiment of a pedicle screw assembly similar to the previous embodiments. The pedicle screw assembly 800 includes a screw seat 802, a "T"-shaped screw 804, an insert 806, a rod holder 808, a retaining ring 810, and a set screw (not shown). The rod holder 808 includes a plurality of distally extending tabs 812 having inwardly directed lips 814. The screw seat 802 includes an annular groove 818 able to receive the lips in snap fitting relationship. The rod holder 808 attaches to the screw seat 802 by pressing the tabs 812 over the screw seat 802 causing the tabs 812 to flex outwardly until the lips 814 engage the groove 818 allowing the tabs to snap inwardly. The retaining ring 810 is pressed onto the rod holder 808 so that it surrounds the tabs 812 and prevents them from flexing outwardly and releasing the screw seat 802.

Figures 26, 27:
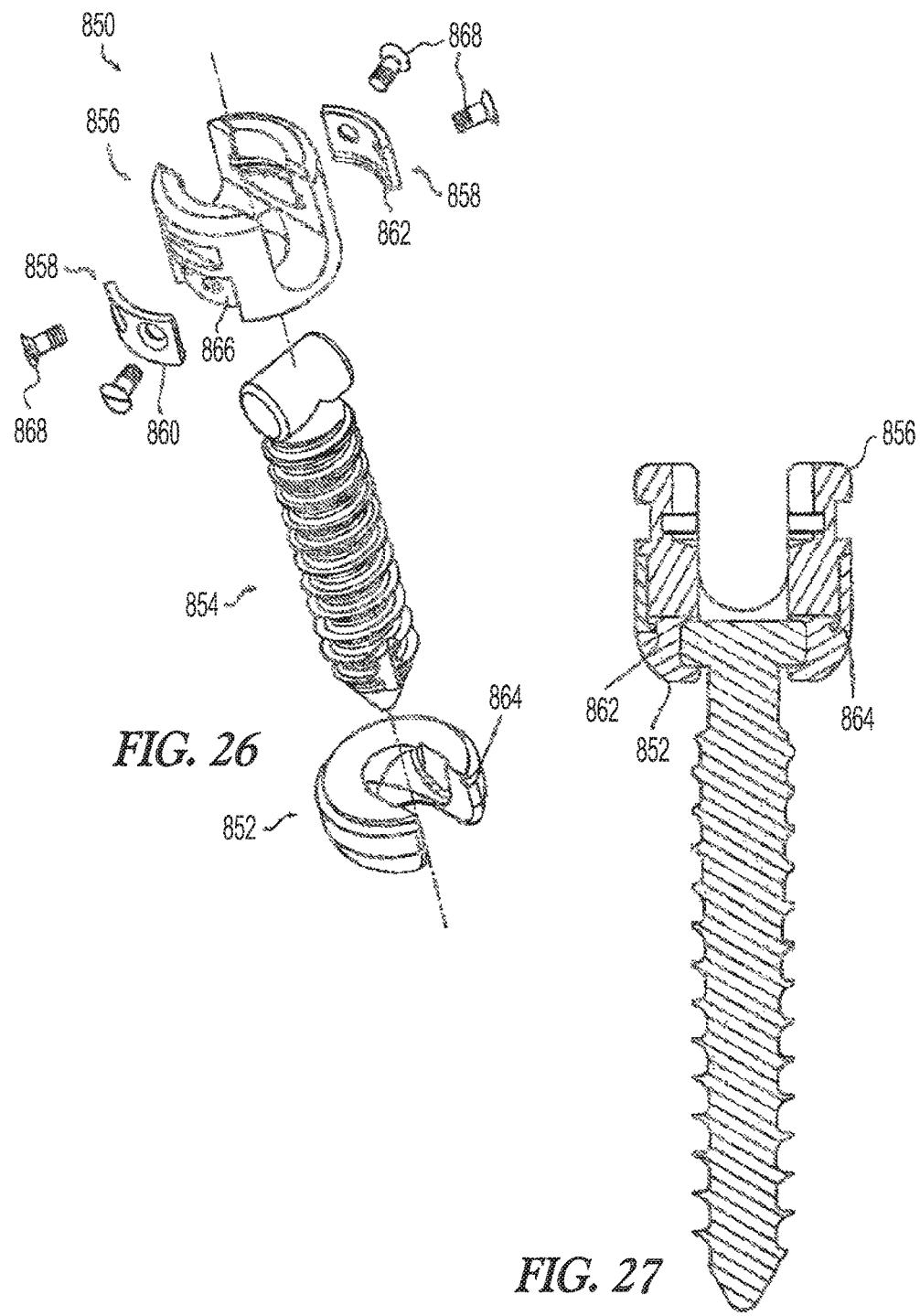
FIG. 26 is an exploded perspective view of another embodiment of a bone fastener assembly according to the present invention.
FIG. 27 is side sectional view of the bone fastener assembly of FIG. 26.

FIGS. 26-27 illustrate the details of another embodiment of a pedicle screw assembly similar to the previous embodiments. The pedicle screw assembly 850 includes a screw seat 852, a "T"-shaped screw 854, a rod holder 856, and a set screw (not shown). One or more plates 858 are provided to attach the rod holder 856 to the screw seat 852. Each plates includes a distally extending portion 860 having an inwardly projecting lip 862. The screw seat 852 includes an annular groove 864 able to receive the lips 862. The plate is attached to the rod holder 856 using a suitable fastening mechanism such as a screw, clip, adhesive, welding, soldering, and or other suitable fastening mechanism. In the illustrative example, two plates 858 are inset into notches 866 formed in opposite sides of the rod holder 856 and screws 868 extend through the plates 858 and thread into the rod holder 856 to attach them to the rod holder 856.

Although examples of a hone fastener assembly and its use have been described and illustrated in detail, it is to be understood that the same is intended by way of illustration and example only and is not to be taken by way of limitation. The invention has been illustrated in the form of a pedicle screw assembly for use in assembling stabilizing constructs to connect vertebrae of the human spine. However, the bone fastener assembly may be configured with other kinds of fasteners and connecting members to assemble other kinds of constructs to stabilize bones and bone fragments at any location in the body. Accordingly, variations in and modifications to the bone fastener assembly and its use will be apparent to those of ordinary skill in the art. The various illustrative embodiments illustrate alternative configurations of various component parts such as screw seats, screws, pivot mechanisms, swivel mechanisms, and inserts among others. In most cases, and as will be readily understood by one skilled in the art, the alternative configuration of a component part in one embodiment may be substituted for a similar component part in another embodiment. For example, the screw seat shown in the embodiment of FIGS. 1-8 may be readily modified with a cylindrical seat to be used with any of the "T"-head screws shown in the embodiments of FIGS. 13-27. Likewise, the various mechanisms illustrated for attaching the screw seat to the rod holder may be interchanged. Furthermore, throughout the exemplary embodiments, where component part mating relationships are illustrated, the gender of the component parts may be reversed as is known in the art within the scope of the invention. The following claims are intended to cover all such modifications and equivalents.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A bone fastener assembly for connecting a bone to a stabilizing construct, comprising:
   a connecting member having a connecting member axis extending from a proximal end to a distal end, a first opening adjacent the proximal end, a second opening adjacent the distal end, and a first spherical surface;
   a one-piece fastener seat having a first end, a second end, a passageway extending from the first end to the second end along a seat axis, and a second spherical surface configured to slidably engage the first spherical surface; and
   a bone fastener having a shank and a head, the shank extending though the passageway, the head engaging a head-mating surface of the fastener seat, wherein the fastener seat is insertable through the first opening and the bone fastener is insertable through the second opening.

2. The bone fastener assembly of claim 1, wherein, the fastener seat being movable from a first position in which the seat axis is transverse to the connecting member axis after the fastener seat and bone fastener are inserted into the connecting member, to a second position in which the seat axis is parallel to the connecting member axis and the fastener seat engages the bone fastener and retains the bone fastener in the connecting member.

3. The bone fastener assembly of claim 2, wherein the fastener seat comprises an outer edge and a notch extending radially outwardly from the passageway to the outer edge to receive the bone fastener as the fastener seat is moved from the first position to the second position.

4. The bone fastener assembly of claim 2, wherein the fastener seat engages the connecting member in the second position in a pivoting relationship such that the fastener seat is able to pivot in at least one vertical plane containing the connecting member axis.

5. The bone fastener assembly of claim 2, wherein the fastener seat engages the connecting member in the second position in a rotating relationship about the connecting member axis and the bone fastener engages the fastener seat in pivoting relationship such that the bone fastener is able to pivot in at least one vertical plane containing the seat axis relative to the fastener seat to vary the angle between the bone fastener and the connecting member.

6. The bone fastener assembly of claim 5, wherein the bone fastener is able to pivot in only one vertical plane containing the seat axis relative to the fastener seat.

7. The bone fastener assembly of claim 6, wherein the bone fastener is able to pivot from a first position in which the shank and the seat axis are parallel, to a second position in which the shank is transverse to the seat axis, the bone fastener being able to pivot in only one direction from the first position.

8. The bone fastener assembly of claim 7, wherein the fastener seat comprises an outer edge and a notch extending radially outwardly from the passageway at least partway toward the outer edge to receive the bone fastener as the bone fastener pivots from the first position to the second position.

9. The bone fastener assembly of claim 1, wherein the head comprises a third spherical surface and the fastener seat comprises a complimentary mating fourth spherical surface.

10. The bone fastener assembly of claim 1, wherein the head comprises a cylindrical surface and the fastener seat comprises a complimentary mating cylindrical surface.

11. The bone fastener assembly of claim 1 wherein the fastener seat comprises an elongated seating surface such that the bone fastener is engageable with the fastener seat in a pivoting relationship at a plurality of spaced apart locations.

12. The bone fastener assembly of claim 1, wherein the head extends radially outwardly on opposite sides of the shank, the head engaging the fastener seat in the second position in a pivoting relationship with one degree of rotational freedom.

13. A bone fastener assembly for connecting a bone to a stabilizing construct, comprising:
   a rod holder having a first passage extending along a first axis from a proximal opening to a distal opening, the passage partially defined by a first surface;
   a one-piece fastener seat having a second passage extending along a second axis from a proximal end to a distal end, the distal end at least partially defined by a second surface configured to mate with the first surface; and
   a bone fastener having a shank for engaging the bone, and a head, the shank defining a fastener axis, the fastener seat and the bone fastener being insertable within the rod holder through opposing openings, the fastener seat being movable along the first surface from a first position in which the second axis is transverse to the first axis after the fastener seat and bone fastener are inserted into the rod holder, to a second position in which the second axis is parallel to the first axis, and the fastener seat engages the bone fastener and retains the bone fastener in the rod holder.

14. The bone fastener assembly of claim 13, wherein the fastener seat is insertable through a first end of the first passage and the bone fastener is insertable through a second end of the first passage.

15. The bone fastener assembly of claim 13, wherein the fastener seat comprises an outer edge and a notch extending radially outwardly from the second passage to the outer edge to receive the fastener as the fastener seat is moved from the first position to the second position.

16. The bone fastener assembly of claim 13, wherein the fastener seat engages the rod holder in the second position in pivoting relationship such that the fastener seat is able to pivot in at least one vertical plane containing the first axis.

17. The bone fastener assembly of claim 13, wherein the fastener seat engages the rod holder in the second position in a rotating relationship about the first axis and the bone fastener engages the fastener seat in pivoting relationship such that the fastener is able to pivot in at least one vertical plane containing the second axis relative to the fastener seat to vary the angle between the bone fastener and the rod holder.

18. The bone fastener assembly of claim 17, wherein the bone fastener is able to pivot in only one vertical plane containing the second axis relative to the fastener seat.

19. The bone fastener assembly of claim 18, wherein the fastener is able to pivot from a first position in which the shank and the second axis are parallel, to a second position in which the shank is transverse to the second axis, the bone fastener being able to pivot in only one direction from the first position.

20. The bone fastener assembly of claim 13, wherein the first and second surfaces are each substantially spherical.

\* \* \* \* \*